United States Patent [19]

Geus et al.

[11] Patent Number: 4,548,921

[45] Date of Patent: Oct. 22, 1985

[54] SILVER CATALYST AND A METHOD FOR THE PREPARATION THEREOF

[75] Inventors: John W. Geus, Bilthoven; Krijn P. de Jong, Utrecht, both of Netherlands

[73] Assignee: Nederlandse Organisatie Voor Zuiver-Wetenschappellik Ondebzoek (zwo), The Hague, Netherlands

[21] Appl. No.: 476,660

[22] Filed: Mar. 18, 1983

[30] Foreign Application Priority Data

Apr. 1, 1982 [NL] Netherlands ......................... 8301398

[51] Int. Cl.$^4$ ....................... B01J 23/14; B01J 23/18; B01J 23/40; B01J 23/50
[52] U.S. Cl. ..................................... 502/330; 502/347
[58] Field of Search ................ 502/243, 330, 347, 348

[56] References Cited

U.S. PATENT DOCUMENTS 3,563,913 2/1971 Krijger et al. ...................... 502/348
4,007,135 2/1977 Hayden et al. ..................... 502/347
4,366,092 12/1982 Winterton ......................... 502/347

FOREIGN PATENT DOCUMENTS 0045620 10/1982 European Pat. Off. .

Primary Examiner—W. J. Shine
Attorney, Agent, or Firm—Jeffrey S. Boone; Norman L. Sims; Christopher John Rudy

[57] ABSTRACT

A silver catalyst comprises a sinter resistant carrier covered with finely divided particles of a metal, a metal alloy or a partially reduced metal oxide having silver deposited thereon such that the outer surface of the particles consists essentially of monometallic silver. The metals are selected from Re, Ru, Os, Rh, Ir, Pd, Pt, Pb and Bi; the metal of the alloy from Re, Ru, Os, Rh, Ir, Pd and Pt; and the oxide from tin dioxide, lead oxide and bismuth oxide. The catalyst is useful in a variety of applications, particularly in the preparation of ethylene oxide.

8 Claims, No Drawings

SILVER CATALYST AND A METHOD FOR THE PREPARATION THEREOF

BACKGROUND OF THE INVENTION

The invention relates to a silver catalyst and to a method for its preparation.

Solid, metallic catalysts are widely employed in a variety of industrial applications such as isomerization, hydrodimerization, hydrogenation, alkylation, oxidation and cyclization. For maximum efficiency, the metallic catalysts are advantageously prepared having a large catalytically active surface area per unit volume of catalyst.

In general, to obtain a desirably high catalytic surface area, the catalytically active component is prepared as finely divided as possible. Unfortunately, at the elevated temperatures normally employed in catalytic operations, most metallic catalysts sinter rapidly, therebvy reducing the catalytically active surface area.

In order to obtain the required thermal stability, the catalytically active component is generally applied to a sinter resistant, inert carrier. Although the inert carrier dilutes the catalyst, the thermal stability provided by the carrier renders the produced supported metal catalysts generally more stable than an unsupported metal catalyst.

It appears to be particularly difficult to apply silver or silver compounds extremely finely divided onto conventional carrier materials such as $SiO_2$ and $Al_2O_3$. For example, it is usual to impregnate the carrier with a solution of the catalytically active material, whereafter the liquid is removed by drying. After drying, the compound is converted into a metal by a thermal treatment, e.g., by gas phase reduction. Unfortunately, impregnation, drying and thermal treatment, using a silver compound, leads to a broad range of silver particle sizes. In addition, to relatively small particles, many very large particles are present.

It has therefore been proposed to deposit the silver from a solution onto the carrier which is suspended in the solution. Thus, in German Offenlegungsschrift No. 1,963,827, a method is proposed in which silver is deposited on a suspended carrier from a dissolved silver complex. This method leads to much better results than impregnation and drying. Silver particles having sizes down to 5 to 20 nm can be applied onto carriers, such as $SiO_2$ or $Al_2O_3$. The smaller of the above sizes is obtained at low loadings of the carrier with silver, whereas higher loadings lead to a larger minimum size. As the silver surface area per unit volume depends on both the size of the individual particles and the particle density, i.e., the silver loading, it is desirable to produce very small supported silver particles at higher loadings.

With other metals it is possible to deposit still smaller particles at high loadings onto carriers. Various metals of Group VIII of the Periodic Table, for example, can be applied to carrier materials as particles of 0.5–1 nm. The present state of art renders this impossible with silver particles at high silver loadings. A support highly loaded with very small silver particles provides a large silver surface area per unit volume and thus exhibits an elevated activity. Consequently, a reaction rate technically required can be obtained at relatively low temperatures. Since especially with oxidation reactions, a better selectivity can be expected at low temperatures, it is important to produce very small supported silver particles.

There is still another difficulty due to the fact that extremely small supported silver particles are not available for technically feasible catalytic reactions. Silver particles having dimensions of minimally 5 to 20 nm are unstable on the conventional carrier materials such as $SiO_2$ and $Al_2O_3$ at higher temperatures. Specifically, the dimension of the silver particles increases relatively rapidly at elevated temperature up to 100 nm or even more. This takes place, either owing to migration by silver particles such as across the carrier surface or by dissociation of silver atoms or ions of the particles, followed by migration to larger silver particles. This undesirable growth of silver particles also occurs, if the starting product comprises small silver particles homogeneously distributed throughout the carrier surface.

In view of the deficiencies of the prior art, a silver catalyst having stable, extremely small silver particles (e.g., about 3 nm) attached to a sinter resistant carrier material and which catalyst does not exhibit the above mentioned deficiencies is required.

SUMMARY OF THE INVENTION

Accordingly, in one aspect, the present invention is such a silver catalyst. Specifically, the catalyst of the present invention is a metallic composite comprising a metal, a metal alloy or an at least partially reduced metal oxide in the form of finely divided particles on the surface of a sinter resistant carrier or support material having silver deposited on said particles, whereby the outer surface of the particles consists essentially of monometallic silver.

The metal, alloy or partially reduced particles serve as an anchoring compound for the silver to the sinter-resistant material. As requirements for the particles that are such anchoring compounds for the silver layer, the following can be mentioned. They must be able to be extremely finely divided on the support in their metallic and/or oxidic form. Further they must exhibit a sufficiently strong bond to the chosen carrier to essentially completely inhibit migration of the particles at conditions of use of the catalyst and they also must exhibit a sufficiently strong adherence to metallic silver to prevent substantially migration of silver particles at conditions of use of the catalyst.

In another aspect, the present invention is a method for preparing the silver catalyst. Said method comprises suspending a carrier whose surface is homogeneously covered with particles of a metal, a metal alloy or at least partially reduced metal oxide in a solution of a silver compound exhibiting an appreciable interaction with the surface of the non-covered carrier material, subsequently reducing the silver compound so as to deposit the silver exclusively on the particles already present and separating the silver laden carrier from the liquid and drying the same. Preferably, the particles are rhenium, a metal of the second or third period of Group VIII metals of the periodic table of elements or an alloy of said metals having a maximum particle size of less than about 10 nanometer or an at least partially reduced metal oxide having a maximum particle size of less than about 25 nanometer.

According to the invention, the reduction of the dissolved silver compound surprisingly proceeds even if the surface of the metal, metal alloy or metal oxide originally present is covered with a thick layer of silver. This means, that although a surface alloy may be formed after the liquid-phase reduction, the reduced silver is not fully absorbed by the anchoring particles originally present, so that, in the catalyst according to the invention, the catalytically active surface is indeed a silver surface.

It has also been found that silver compounds can be reduced in such a manner that the metallic silver is deposited solely onto the particles of the anchoring compound, whereas reduction does not proceed in the liquid proper or on the uncovered carrier surface. The result is that the silver is essentially exclusively deposited at the anchoring particles previously present on the carrier surface. Thus the process according to the invention provides thermally stable silver surfaces.

The metal catalysts of this invention exhibit exceptional thermal stability and are useful as catalysts in a variety of industrial applications including isomerization, hydrodimerization, alkylation, cracking, dehydrocyclization, oxidation and cyclization. The monometallic surface catalysts of the present invention are particularly useful in the preparation of the ethylene oxide by the oxidation of ethylene.

DETAILED DESCRIPTION OF THE PREFERRED EMBODIMENTS

Examples of metals or metal oxides to be used as anchoring compounds on the carrier are lead, lead oxide, bismuth and bismuth oxide. Preferably, if a metal is used for the anchoring compound, it is rhenium or a metal selected from the second or third period of the Group VIII metals of the Periodic Table, or an alloy of said metals. The metals of the second or third period of Group VIII of the Periodic Table include platinum, palladium, iridium, rhodium, osmium and ruthenium. The Group VIII metals most preferably employed are those metals which do not form with silver a continuous solid solution, but exhibit a limited solubility, with platinum being the most preferred. If the particles consist of an at least partially reduced metal oxide, preferably reduced tin dioxide is used. In the case that the particles consist of a metal or an alloy, the particle size is preferably maximum about 10 nanometer, whereas in the case the particles consist of an at least partially reduced metal oxide, the particle size is preferably maximally about 25 nanometer.

The carrier or support material is suitably any normally solid material onto which the metal or metal oxide, in particular rhenium or the Group VIII metal, can be deposited in a finely divided form, e.g., at an average particle size of less than about 5 nanometer in the case of rhenium and the Group VIII metals and at a particle size of less than about 20 nanometer in the case of the (partially) reduced metal oxide.

The carrier material most advantageously employed in the practice of the present invention is dependent on a variety of factors including its surface area, porosity and pore size. In general, carrier materials conventionally employed heretofore in the preparation of solid, metallic catalysts are advantageously employed in the preparation of the metallic catalyst of the present invention, provided that the solution of the silver compound to be used exhibits an appreciable interaction with the surface of the carrier. Representatives of such carrier materials are silicon dioxide ($SiO_2$), aluminium oxide ($Al_2O_3$), ion exchange zeolites and the like. The most advantageous combination of particles and support can easily be determined by the skilled artisan.

The metal or metal oxide can be deposited in the form of finely divided particles by any of a variety of techniques well known in the art. For example, the support material can be impregnated with a solution of a metal salt followed by the evaporation of the solvent. Another method for incorporating the metal on the surface of the support consists of depositing the metal from a solution thereof by precipitation through a chemical reaction. Yet another method for depositing the metal on the carrier material involves liquid-phase reduction of metal ions to a metallic state in an aqueous suspension of the support. Illustrative of these and other methods for depositing the metal on the carrier material are described in "Structure of Metallic Catalysts", by J. R. Andersson, Academic Press, London (1975).

In the practice of the present invention, the silver is deposited on the carrier whose surface is homogeneously covered with finely divided particles of an anchoring compound as earlier defined by suspending it into a solution of silver compound exhibiting an appreciable interaction with the surface of the non-covered material, after which the silver compound is reduced so as to deposit the silver exclusively on the particles of the anchoring compound already present and the silver-laden carrier is separated from the liquid and dried.

According to a preferred embodiment of the invention, the catalyst so obtained is subjected to an oxidizing treatment at elevated temperature. By this oxidation, the distribution of silver over the surface of the particles of the anchoring compound is made uniform and with thin silver layers a surface alloy that might have been formed is decomposed into a pure silver layer.

Because in many catalytic reactions the selectivity of silver alloy is inferior to that of pure silver surfaces, sufficient silver must be deposited on the particles of the anchoring compound originally present, so that, as prepared or after the oxidation, if required, a monometallic silver surface is obtained. That it is possible to deposit sufficient silver on the surface without the formation of large, pure silver particles by reduction in the liquid or on the uncovered carrier, is surprising.

Dutch Patent Application No. 73.16236 discloses that certain compounds can be selectively reduced on surfaces of noble metals. The result of this prior process is the formation (surface) alloy of the reduced material with the metal originally present. This method has been used in particular with metal powders, such as Pd-black, where no carrier is present. Indeed, the requirement that the material to be reduced must exhibit a sufficiently strong interaction with the surface of the pure carrier has not been appreciated. In addition, in the described process, the reduction of the dissolved material becomes very slow when approximately a monolayer of reduced atoms is deposited on the surface of the noble metal particles originally present.

As the examples of the mentioned application show, it is possible to deposit more than a monolayer of Ge on Pd and Ru. This is caused by the fact that the Ge deposited on the surface is slowly dissolved in the palladium or ruthenium with the formation of an alloy. The result is that the Pd or Ru is again partially exposed, and fresh Ge can be deposited on the metal. The dissolution of Ge proceeds very slowly. As a consequence, the reduction must be continued for 100 hours for an amount corresponding to approximately 6 monolayers to be incorporated in the Ru lattice.

In the Examples IV and V of the application, the reduction process is continued for a long time (approx.

50 hours) for the Pd to absorb Ge or Sb to an appreciable extent. From this, it can indeed be concluded that the reduction of the dissolved component only proceeds on the noble metal surface. When the noble metal surface is fully covered with Ge or Sb the reduction stops. It is only if, from diffusion of the Ge or Sb into the noble metal atoms under the formation of an alloy, that the noble metal atoms at the surface are again exposed and Ge or Sb is again reduced. A similar observation can be made about Example II of Dutch Patent Application No. 73,16326, in which rhenium is caused to be incorporated by ruthenium and whereby it was found that the rhenium had been fully incorporated by the ruthenium. In addition, the disclosed prior art method can result in the undesirable formation of larger metal particles in the liquid phase. Formation of large particles is generally observed with a metal ion that can be reduced rather easily. After deposition of a relatively small amount onto the surface of the metal particles, growth of large particles proceeds in the solution. An example for the growth of the large particles is gold.

It has surprisingly been found that the desired result is obtained only if a silver-containing dissolved compound is utilized that exhibits an appreciable interaction with the surface of the support material. The expression "appreciable interaction" means, that the electrostatic charges of the silver compound and the surface of the support are favourable and that the silver compound is hence markedly attracted by the support. If an acid reacting support such as $SiO_2$, which at pH levels above 2 is negatively charged, is used, positively charged complexes of silver such as $Ag(NH_3)_2^+$ are advantageously employed. When employing an alkaline reacting support such as $Al_2O_3$, which generally is positively charged above pH levels of about 7, negatively charged silver compounds such as Ag-EDTA are preferably employed.

In preparing the catalyst, the silver-containing compound is advantageously employed in amounts sufficient to essentially completely cover the surface of the anchoring particles with metallic silver upon subsequent reduction of the silver.

Such amounts will vary depending on a variety of factors including the specific anchoring particles employed and the desired properties of the resulting catalyst. For example, if the metal in the anchoring particles forms an alloy with silver, generally greater amounts of the silver-containing compound are employed. Specifically, although an alloy of the silver with a Group VIII metal can be initially formed upon the deposition of the silver on the metal surface, sufficient additional amounts of the silver are employed such that upon further decomposition, a composite having a surface, comprising monometallic silver is obtained. In the case when an oxide is used as anchoring particle, generally less amounts of silver compound can be used.

The solution of the silver-containing compound is preferably a solution of the silver-containing compound dissolved in an aqueous liquid. By the term "aqueous liquid" it is meant water (including aqueous liquids such as alkaline or acidic aqueous solutions or aqueous salt solutions) or a solution of water with a water miscible liquid, preferably a polar liquid such as a lower alcohol, e.g., methanol, ethanol or propanol; a lower ketone, e.g., acetone or methyl ethyl ketone; an ether, e.g., diethylether or the like. Less preferably, organic liquids in which a suitable silver-containing compound is soluble can be employed.

Any reducing agent capable of reducing the unreduced silver compound can be employed in the subsequent reduction of silver and deposition of the metallic silver on the surfaces of the metal or metal oxide initially deposited. Both gaseous reducing agents and liquid reducing agents which are soluble in the silver-containing solution can be employed.

Representative gaseous reducing agents include hydrogen, carbon dioxide, inert gases containing hydrogen and the like; with hydrogen being preferred. Representative liquid reducing agents include hydrazine, hydroxyl amine, formaldehyde and glucose, with hydrazine and formaldehyde being preferred. In general, the liquid reducing agents are more preferably employed in the practice of the present invention.

The silver is reduced at conditions such that metallic silver is deposited essentially exclusively at the anchoring metal or metal oxide particles previously applied. For the purposes of this invention, the silver is presumed to be essentially exclusively deposited on the anchoring compound when essentially no silver particles are formed in the liquid phase during reduction. preferably less than 2, more preferably less than one, weight percent of the reduced silver will form as particles in the liquid phase during reduction of the silver.

The conditions most advantageously employed for reducing the silver are dependent on a variety of factors including the specific anchoring compound employed, the specific reducing agent and silver compound employed, as well as the properties of the carrier and the desired properties of the resulting catalyst composite and the temperature of the resulting solution. In general, when using a gaseous reducing agent, the reducing gas is bubbled through the stirred, silver-containing liquid solution having the anchoring particles on the carrier suspended therein. When employing a liquid reducing agent, the liquid reducing agent, either neat or in solution with a miscible liquid, is slowly added to the stirred silver-containing solution, so as to avoid high local concentrations of the reducing agent in the liquid. The reduction of the silver is conducted at a temperature sufficient to cause deposition of silver essentially exclusively at the surface of the anchoring compound, without the formation of significant amounts of silver-metal particles in the bulk medium of the solution.

The adjustment of the temperature is a highly suitable means to effect that reduction only takes place on metal particles previously applied. For example, from a given temperature upwards, reduction in the liquid or on the pure carrier surface often proceeds whereas at lower temperatures reduction is limited to the metal particles previously applied. Although such temperatures will, as said, vary depending on the reducing agent, anchoring metal and the silver compound employed, in general, temperatures up to the boiling point of the liquid are advantageously employed herein.

The reduction of the silver is continued until the desired amounts of metallic silver are deposited on the surface of the Group VIII metal. The amounts of the deposited metallic silver are easily determined using an ion-selective elctrode which measures the concentration of the silver in solution (the decrease in the concentration of silver ions in solution from which can be determined the amounts of silver subsequently deposited on the surface of Group VIII metal). In general, the reduction of the silver is allowed to continue for from 0.5 to 2 hours. To prevent reoxidation of the metallic silver deposited on the anchoring compound, the reduction is preferably conducted in an oxygen free atmosphere.

Upon completion of the reduction reaction, the resulting composite which now comprises the Group VIII metal having silver on its surface, is separated—preferably in an oxygen free atmosphere—from the liquid reduction medium and dried at elevated temperatures from 20° to 200° C. for periods sufficient to make the composite sensibly dry, i.e., dry to touch. The resulting composite can be used as prepared. Optionally, but preferably, the resulting composite is oxidized at an elevated temperature subsequent to drying. Such oxidation unexpectedly distributes the silver more uniformly over the metal surface. Such oxidation is preferably conducted by contacting the resulting composite with an oxygen-containing gas, e.g., air, at temperatures from 200° to 550° C. for periods of at least 0.5 hours.

The following examples are set forth to illustrate the advantages of this invention and should not be construed to limit its scope.

EXAMPLE 1

Using conventional precipitation techniques, platinum (Pt) is deposited on a silicon dioxide ($SiO_2$) carrier material in a finely divided particulate form having a surface mean particle size of 23 A. Sufficient amounts of the Pt are deposited such that the resulting $Pt/SiO_2$ combination contained 6 weight percent Pt based on the total weight of the combination. The BET surface of the combination is measured as 189 square meters ($m^2$)/gram(g) and at room temperature, the catalyst is found to absorb 3.30 milliliters (ml) $H_2$/g of catalyst.

An aqueous solution of $10^{-2}$ mole/liter $Ag(NH_3)_2$ is prepared. To 100 g of the solution is added about 5 g of the platinum/silicon dioxide combination. To the resulting mixture is added 1.2 g of an aqueous solution of 37 weight percent formaldehyde, dissolved in 100 ml water, which corresponds to about 4 g of reducing agent per gram of dissolved silver. The whole amount of reducing agent is added in a period of 1 minute. During and subsequent to this addition, the aqueous solution of the dissolved, unreduced silver compound is agitated and maintained at a temperature of 5° C.

The reduction caused by the formaldehyde takes place rapidly as evidenced by the rapid decrease of the silver concentration in the aqueous solution, with essentially all the silver ions being reduced after a period of about 60 minutes. At this time, the resulting composite which consists of Ag coated $Pt/SiO_2$ is removed from the solution and dried at 120° C. for a period of 16 hours.

Upon examination of the dried composite under a transmission electron microscope, the composite shows irregularly shaped metal particles, sometimes rod-like, due to the deposition of the metallic silver exclusively adjacent to the regularly shaped platinum particles. The final composite comprises 2 weight percent silver based on a total weight of the composite and about 38 atomic percent silver based on the total atoms of the silver and platinum. The number average particle size of the silver coated platinum particles as determined by transmission electron microscopy is 3 nanometer.

EXAMPLE 2

Using similar techniques as employed in Example 1 silver is deposited on a $Pt/SiO_2$ combination to form a solid, metallic silver catalyst which comprises about 5.5 weight percent silver based on the total weight of the catalyst composite and about 64 atomic percent silver based on the total number of atoms of platinum and silver in the composite. This composite is found, when examined under a transmission electron microscope, to have number average particle size of about 5 nanometer. To demonstrate the effectiveness of the present invention in completely covering the platinum particles with silver, the infrared spectra of carbon monoxide absorbed on the catalyst composite is measured. The absorption band at 2090 $cm^{-1}$ is due to the carbon monoxide absorbed on the non covered platinum sites. The intensity if the 2090 $cm^{-1}$ band is 0.08. This compares favourably with a carbon monoxide absorbance of the $Pt/SiO_2$ combination of about 1.68 at 2090 $cm^{-1}$. This absorbance data confirms the fact that only minimal amounts of the platinum surface are uncoated with silver.

EXAMPLE 3

A silver catalyst is prepared using similar techniques to those employed in preparing the catalyst of Example 2, except that the aqueous solution of formaldehyde is added continuously over a period of 30 minutes. The resulting catalyst is found to comprise about 5.7 weight percent silver based on the total weight of the silver catalyst and have a particle size of about 3 to 10 nanometer.

EXAMPLE 4

A silver catalyst is prepared using techniques similar to those of Example 3 except that silver comprises only 1.5 weight percent of the final catalyst composite. The carbon monoxide absorbance of this catalyst at 2090 $cm^{-1}$ is shown to be 0.61 which indicates that greater amounts of the platinum surfaces are not coated with silver than the catalyst prepared in Examples 1-3. However, the catalyst is still usable in many commercial chemical processes and is an example of the present invention.

EXAMPLE 5

Using the method of Example 3, a silver catalyst is prepared using hydrazine as the reducing agent, but at a temperature of the reaction solution of 4.5° C. The final catalyst is found to contain 5,3 weight percent silver based on the total weight of the catalyst composite. The carbon monoxide absorbanee of the catalyst at 2090 $cm^{-1}$ is only 0,31, indicating that significant portions of the platinum are covered by the silver. By changing the conditions at which reduction takes place, e.g., changing the temperature at which reduction is conducted or changing the rate of hydrazine addition, the coverage of the platinum particles can be varied with a coincident variation of the amount of silver particles formed in the aqueous solution. The reason for this is, that hydrazine is such a fast reducing agent, that in principle it can produce silver both on the platinum particles and in the liquid phase.

EXAMPLE 6

In this Example, tin oxide has been employed as the anchoring compound by finely dividing the tin oxide onto $SiO_2$ according to the method described in the Dutch Patent Application No. 6712004.

In order to obtain this, 46.6 g $SnCl_4.5H_2O$ and 80 g urea were dissolved in 1 l water. Thereafter, 20 g $SiO_2$ (AEROSIL 200 V, Degussa) with a surface of about 200 $m^2$/g was suspended into the solution. The suspension was kept for a period of 7 hours at a temperature of 90° C. while providing continuously agitation. During this time period, the pH value was increased to about 6 and the tin (IV) completely deposited on the carrier. The loaded carrier was separated from the liquid and rinsed thoroughly until the rinsing water no longer contained chloride ions. After calcination at 450° C. the loaded carrier contained about 50 weight percent $SnO_2$. Examination of the loaded carrier using an electron microscope showed that the $SnO_2$ was deposited homogeneously as particles of about 1 nm on the carrier surface.

The thus loaded carrier was first ground in a ball-mill and afterwards suspended into an aqueous solution containing about $10^{-2}$ mole/l of $Ag(NH_3)_2^+$. The silver was precipitated similarly to Example 1 by reduction with formaldehyde at 5° C. It was found that the silver deposited onto the anchoring particles in particulates smaller than 5 nm. In practice, the thus obtained catalyst proved to be very thermally stable. Calcination at a temperature higher than 400° C. did not increase the size of the silver particles.

COMPARATIVE EXAMPLE I

In this Example it is demonstrated, that a positive interaction between the dissolved silver complex and the surface of the pure support is required to obtain formation of small silver particles on the surface of the support. In this example, silver ions not strongly interactive with the silica surface are employed.

A silicon dioxide support material identical to those employed in Examples 1-5 is placed in an aqueous solution containing silver ions. The attempted reduction of the silver ions generally leads to the formation of very large silver particles in the liquid phase which do not adhere to the support structure. This is believed to be due to the weak interaction between the deposited silver ions and the carrier metarial and the relatively high concentration of silver ions in solution.

COMPARATIVE EXAMPLE II

In this Example a complex, strongly interacting with the surface is used.

To prepare silver catalyst on a $SiO_2$ support material without the intermediate anchoring metal, an aqueous solution of a complex of silver and ammonia, $Ag(NH_3)_2+$ is prepared and an $SiO_2$ support material (identical to the support employed in Examples 1-5) is suspended in the aqueous solution. The reduction of the silver is carried out with formaldehyde as the reducing agent at temperatures of 50° C. for a period of 60 minutes.

Owing to the interaction of the silver complex with the support, a small fraction of the silver has been deposited at a desirably small particle size on the surface of the support. Since the catalyzing effect of the anchoring compound was not present, a large proportion of the silver has precipitated as large particles (40-100 nm) in the bulk of the solution. Although silver is deposited on the carrier material, the wear interactions between the metal and the support allows for high mobility of the silver with a coincident formation of particles having a large particle size, thereby making the catalyst material unsuitable for commercial operations.

What is claimed is:

1. A silver catalyst comprising finely divided particles of a metal, metal alloy or an at least partially reduced metal oxide, said metal selected from rhenium, ruthenium, osmium, rhodium, iridium, palladium, platinum, lead, or bismuth; the metal of said alloy selected from rhenium, ruthenium, osmium, rhodium, iridium, palladium or platinum; said metal oxide selected from tin dioxide, lead oxide or bismuth oxide; on the surface of a sinter resistant carrier and silver deposited on said particles, the outer surface of the particles consisting essentially of monometallic silver.

2. The silver catalyst of claim 1 wherein the finely divided particles are rhenium, a metal of the second or third period of the Group VIII metals of the Periodic Table of Elements or an alloy of said metals which particles have a particle size of maximally about 10 nanometer.

3. The silver catalyst of claim 1 wherein the finely divided particles are at least partially reduced tin dioxide which particles have a maximum particle size of less than about 25 nanometer.

4. The silver catalyst of claims 1, 2, or 3 wherein the carrier is a sinter resistant oxidic material.

5. A method for preparing the catalyst of claim 1, said method comprising the steps of suspending a carrier whose surface is homogeneously covered with particles of a metal, a metal alloy or an at least partially reduced metal oxide in a solution of a silver compound exhibiting an appreciable interaction with the surface of the non-covered carrier material, subsequently reducing the silver compound so as to deposit the silver exclusively on the particles already present and separating the silver laden carrier from the liquid and drying same.

6. The method of claim 5 wherein the particles are rhenium, a metal of the second or third period of Group VIII metals of the Periodic Table of Elements or an alloy of said metals having a maximum particle size of less than about 10 nanometer or an at least partially reduced metal oxide having a maximum particle size of less than about 25 nanometer.

7. The method of claim 6 wherein the reduction of the silver compound and the separation of the silver laden carrier from the liquid is carried out in an oxygen free atmosphere.

8. The method of claim 7 wherein the catalyst, after drying, is subjected to an oxidizing treatment at elevated temperature.

* * * * *